(12) United States Patent
Ma et al.

(10) Patent No.: US 11,644,584 B2
(45) Date of Patent: May 9, 2023

(54) GAMMA RADIATION IMAGING DEVICE AND IMAGING METHOD THEREOF

(71) Applicant: Tsinghua University, Beijing (CN)

(72) Inventors: Tianyu Ma, Beijing (CN); Yaqiang Liu, Beijing (CN); Xuewu Wang, Beijing (CN); Zhong Wang, Beijing (CN)

(73) Assignee: Tsinghua University, Beijing (CN)

( * ) Notice: Subject to any disclaimer, the term of this patent is extended or adjusted under 35 U.S.C. 154(b) by 145 days.

(21) Appl. No.: 17/415,578

(22) PCT Filed: Nov. 28, 2019

(86) PCT No.: PCT/CN2019/121615
§ 371 (c)(1),
(2) Date: Jun. 17, 2021

(87) PCT Pub. No.: WO2020/125371
PCT Pub. Date: Jun. 25, 2020

(65) Prior Publication Data
US 2022/0066056 A1 Mar. 3, 2022

(30) Foreign Application Priority Data

Dec. 19, 2018 (CN) .......................... 201811559943.2

(51) Int. Cl.
*G01T 1/29* (2006.01)
*G21K 1/02* (2006.01)
(52) U.S. Cl.
CPC .............. *G01T 1/2907* (2013.01); *G21K 1/02* (2013.01); *G01T 1/2985* (2013.01)

(58) Field of Classification Search
CPC ........ G01T 1/2907; G01T 1/2985; G21K 1/02
See application file for complete search history.

(56) References Cited

U.S. PATENT DOCUMENTS

| 4,037,105 A | 7/1977 | Laurer |
| 5,665,970 A * | 9/1997 | Kronenberg ............. G01T 1/18 |
| | | 250/361 R |

(Continued)

FOREIGN PATENT DOCUMENTS

| CN | 101806912 A | 8/2010 |
| CN | 103558626 A | 2/2014 |

(Continued)

OTHER PUBLICATIONS

"International Search Report and Written Opinion of the International Searching Authority", International Application Mo. PCT/CN2019/121615, dated Mar. 6, 2020, 8 pp.

(Continued)

*Primary Examiner* — Hugh Maupin
(74) *Attorney, Agent, or Firm* — Myers Bigel, P.A.

(57) ABSTRACT

The present disclosure provides a gamma ray imaging device and an imaging method, where the imaging device includes a plurality of separate detectors. The plurality of separate detectors are provided at an appropriate spatial position, in an appropriate arrangement manner and are of an appropriate detector material, such that when rays emitted from different positions in an imaging area reach at least one of the plurality of separate detectors, at least one of the thicknesses of the detectors, the materials of the detectors, and the numbers of the detectors though which the rays pass are different, thereby achieving the effect of determining the directions of rays.

19 Claims, 3 Drawing Sheets

(56) References Cited

U.S. PATENT DOCUMENTS

| | | | |
|---|---|---|---|
| 9,606,245 | B1 | 3/2017 | Czarnecki et al. |
| 9,784,850 | B2 | 10/2017 | Da Silva Rodrigues et al. |
| 10,371,830 | B2 | 8/2019 | Jacobs et al. |
| 10,524,748 | B2 | 1/2020 | Freesmeyer |
| 2004/0001570 | A1 | 1/2004 | Kuroda et al. |
| 2010/0301221 | A1 | 12/2010 | Nakamura |
| 2016/0209515 | A1 | 7/2016 | Da Silva Rodrigues et al. |
| 2017/0119327 | A1 | 5/2017 | Freesmeyer |
| 2018/0172848 | A1 | 6/2018 | Nelson et al. |
| 2018/0275289 | A1 | 9/2018 | Jacobs et al. |
| 2021/0290196 | A1* | 9/2021 | Rodrigues ............ A61B 6/4275 |

FOREIGN PATENT DOCUMENTS

| | | | |
|---|---|---|---|
| CN | 104793231 | A | 7/2015 |
| CN | 105011959 | A | 11/2015 |
| CN | 108139491 | A | 6/2018 |
| CN | 109009198 | A | 12/2018 |
| DE | 10318416 | A1 | 11/2003 |
| JP | 2009063589 | A | 3/2009 |
| JP | 2009257962 | A | 11/2009 |
| JP | 2013200164 | A | 10/2013 |
| JP | 2016533477 | A | 10/2016 |
| JP | 2017524408 | A | 8/2017 |
| RU | 2014139064 | A | 4/2016 |
| WO | 2008139625 | A1 | 11/2008 |
| WO | 2015044019 | A1 | 4/2015 |

OTHER PUBLICATIONS

"Communication with Supplementary European Search Report", EP Application No. 19900092.8, dated Dec. 14, 2021, 9 pp.

"First Chinese Office Action", corresponding to CN 201811559943.2, dated Mar. 23, 2022, (14 pages, including English translation).

Examination report for AU application No. 2019411375 dated Jun. 23, 2022, 5 pages.

First Office Action for corresponding EP application No. 19900092.8 dated Mar. 1, 2023, 8 pages.

Office Action for corresponding CA application No. 3,123,980 dated Aug. 19, 2022, 4 pages.

Office Action for corresponding JP Office Action No. 2021-535274 dated May 10, 2022, with translation, 10 pages.

Office Action for corresponding RU application 2021121141/28(044331) dated Dec. 21, 2021, 2 pages.

* cited by examiner

GAMMA RADIATION IMAGING DEVICE AND IMAGING METHOD THEREOF

CROSS-REFERENCE TO RELATED APPLICATION(S)

This application is a Section 371 National Stage Application of International Application No. PCT/CN2019/121615, filed on Nov. 28, 2019, entitled "GAMMA RADIATION IMAGING DEVICE AND IMAGING METHOD THEREOF", which claims priority to Chinese Patent Application No. 201811559943.2, filed on Dec. 19, 2018, which are incorporated herein by reference in their entirety.

TECHNICAL FIELD

The present disclosure relates to the field of nuclear technology and application technology, and in particular to a gamma radiation imaging device and imaging method thereof.

BACKGROUND

Gamma radiation imaging is widely used in medical diagnosis, nuclear leakage and nuclear radiation hot spot monitoring, nuclear waste management, industrial and agricultural radioactive source management and monitoring. The gamma radiation imaging device is used to detect the nuclide that emits gamma photons and form an image of its spatial distribution. It may be used independently as an industrial gamma camera, or as a gamma camera for medical diagnosis, or as key functional components of single-photon emission computed tomography (SPECT) or positron emission computed tomography (PET).

Gamma radiation imaging devices generally include a detector and a collimator. Where the detector part adopts a position-sensitive gamma detector to obtain the position information, energy information and time information of the photons incident on the detector, which may be a scintillation detector composed of a scintillation crystal+photomultiplier tube, or a semiconductor detector, or other detectors that may be used for gamma radiation measurement. The collimator is disposed between the detector and the object to be detected. It only allows photons in a certain direction to be incident on the detector and absorb photons in other directions. Combining the position of the photons detected on the detector and the incident direction of the photons allowed by the collimator, the path information of the photons emitted from the human body may be obtained to form a plane gamma radiation source distribution image. It is also possible to use the detector and collimator to rotate around the object to be imaged, measure multiple plane gamma images in multiple directions, and obtain three-dimensional gamma radiation source distribution images by using tomographic reconstruction algorithms.

The collimator of the gamma radiation imaging device adopts the principle of absorption collimation. That is, a collimator is made of heavy metals such as lead and tungsten. The collimator is provided with holes, slits, grooves and other gaps. The photons that enter the gaps pass through the collimator and are detected by the detector. Other photons are blocked and absorbed by the collimator. Typically there are parallel-hole collimators, fan-beam collimators, pinhole collimators, etc. The collimator made in this way blocks most of the photons and allows only a small part of the photons to be passed through, so that the photon events received on the detector unit may only come from a smaller area in the space of the object to be imaged, and images with higher spatial resolution may be obtained through image reconstruction algorithms. However, as a large number of photons are absorbed, the detection efficiency is very low, which seriously affects the imaging performance.

The gamma radiation imaging device based on the coded aperture collimator greatly improves the aperture ratio on the collimator. A large number of photons incident from radiation sources in different directions form different projection plane distributions on the detector and the image reconstruction algorithm is used to solve the direction of the radiation sources. Although the detection efficiency of this kind of collimator is greatly improved, the photon events received on the detector unit may come from multiple areas or a larger area in the space of the object to be imaged, and the direction information that may be obtained from a single photon is significantly reduced, only suitable for imaging of specific distributions such as spot or sparse radioactive sources. In scenes such as nuclear medicine imaging, due to the wide and continuous distribution of radiopharmaceuticals in the human body, the imaging effect is worse than that of gamma cameras with low detection efficiency based on parallel-hole collimators and other collimators.

In summary, as the collimator of the traditional gamma radiation imaging device adopting the absorption collimation principle absorbs a large number of photons, the detection efficiency of the imaging device is very low, which makes the acquisition time long, or the image quality in the limited acquisition time is poor. The coded aperture collimator with high aperture ratio improves the detection efficiency, but reduces the directional information carried by the received photon events, and its image quality has not been improved accordingly.

SUMMARY

The present disclosure provides a gamma radiation imaging device with separate detectors and an imaging method. By separating the detectors into multiple units in space, and placing different detector units in sequence along the movement direction of the photons, a detector unit located in front along the movement direction of the photons may block and collimate photons for a detector unit following the detector unit. With the different detector units made of detector materials with different attenuation ratios to photons, the different detector units located in the front along the movement direction of the photons may block and collimate different photons for a detector unit following the different detector units, so as to realize the effect of determining the direction of the photons.

The photon events measured by all the detector units in the above device (including the detector units that have collimating effect on other detectors) may be applied to any imaging method, thereby improving the detection efficiency and increasing the directional information carried by the photon events, resulting in higher quality images.

According to one aspect of the present disclosure, there is provided a gamma ray imaging device, including: a plurality of separate detectors, wherein rays emitted from different positions in an imaging area reach at least one of the plurality of separate detectors through different sets of one or more other detector of the plurality of separate detectors, the sets of one or more other detector are different in at least one of thickness of detector, material of detector, and number of detectors.

According to another aspect of the present disclosure, there is provided an imaging device, including: a plurality of separate detectors, the plurality of separate detectors form a plurality of detector layers arranged outside an object to be detected, wherein two adjacent detector layers are spaced from each other by an interval.

According to yet another aspect of the present disclosure, there is provided an imaging device including: a plurality of separate detectors, the plurality of separate detectors comprise at least two types of detectors, the plurality of separate detectors form a plurality of detector layers arranged outside an object to be detected, and the imaging device further comprises a collimator located between the object to be detected and an innermost detector layer along movement direction of photons.

According to another aspect of the present disclosure, there is provided an imaging method, including: providing a plurality of separate detectors, arranging the plurality of separate detectors in form of multi-layers outside an object to be detected to form a plurality of detector layers; imaging the object to be detected by using the plurality of detector layers; wherein rays emitted from different positions in an imaging area reach at least one of the plurality of separate detectors through different sets of one or more other detector of the plurality of separate detectors, the sets of one or more other detector are different in at least one of thickness of detector, material of detector, and number of detectors.

According to another aspect of the present disclosure, there is provided an imaging method, including: providing a plurality of separate detectors, arranging the plurality of separate detectors in form of multi-layers outside an object to be detected to form a plurality of detector layers, wherein two adjacent detector layers are spaced from each other by an interval; imaging the object to be detected by using the plurality of detector layers.

According to another aspect of the present disclosure, there is provided an imaging method, including: providing a collimator and at least two types of a plurality of separate detectors; arranging the plurality of separate detectors in form of multi-layers outside an object to be detected to form a plurality of detector layers; disposing the collimator between the object to be detected and a detector layer located innermost along movement direction of photons; imaging the object to be detected by using the plurality of detector layers and the collimator.

<Symbol Description>

Figure 1:
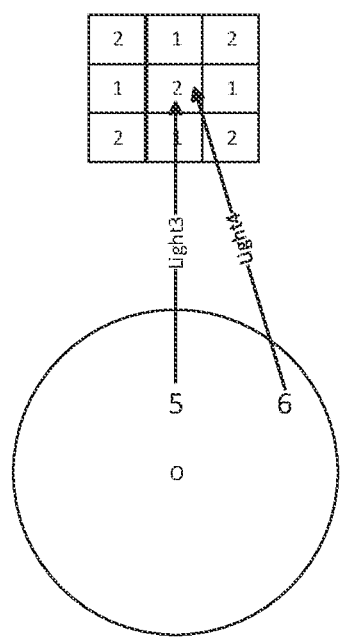
FIG. 1 is a schematic structural diagram of a gamma radiation imaging device according to an embodiment of the disclosure.

1—the first type of detector, 2—the second type of detector, 3,4—light, 5,6—position, 7—collimator, O—object to be detected.

DETAILED DESCRIPTION OF EMBODIMENTS

In order to make the objectives, technical solutions and advantages of the present disclosure clearer, the present disclosure will be further described in detail below in conjunction with specific embodiments and with reference to the accompanying drawings.

The present disclosure proposes to use a detector capable of detecting scintillation photons to form a collimator of a gamma radiation imaging device. The collimator part may be composed entirely of detectors that may detect scintillation photons, or may be composed of any existing collimator and a detector that may detect scintillation photons. Any detector in the detector part may be used as a collimator of other detectors, or may only operate as a detector. Through proper detector structure, material, arrangement relationship, etc., at least one of the thicknesses of the detectors, the materials of the detectors, and the numbers of detectors that the rays emitted from different positions in the imaging area reach the same detector are different (for example, for any detector a, before the ray b and ray c emitted from different positions in the imaging area reaching the detector a, the thicknesses of the detector passed through are different, and/or the materials of the detector passed through are different, and/or the numbers of detectors passed through are different), so that the position of the ray emitted may be determined by measuring the intensity of the ray in the detector, and an image may be obtained.

In order to further enhance the collimator effect of the detector used as a collimator, the detector may be composed of a variety of detector materials, so that the detectors at different positions in space may have different photon (ray) attenuation ratios (attenuation coefficients). The rays from different directions incident on a certain detector have different attenuation ratios because they pass through different detector materials on their paths, and thus the purpose of determining the direction of photons may be achieved.

In order to further enhance the collimator effect of the detector used as a collimator, the detectors may be arranged non-closely in space. By changing the distance between the detectors, the distance between adjacent layers is equal to or greater than the size of the detector, or the distance between adjacent detectors on the same layer is equal to or greater than the size of the detector, so that the rays from different directions incident on a certain detector have different attenuation ratios because they pass through different other detectors on their paths, and thus the purpose of determining the direction of photons may be achieved.

In this manner, the present disclosure provides a gamma radiation imaging device and imaging method that not only has high photon detection efficiency, but also high photon events information, so as to solve at least one of the above problems.

Embodiment 1

In this embodiment, as shown in FIG. 1, the imaging device includes 9 detectors, and the 9 detectors form 3 detector layers, which are distributed in 3 layers outside the object to be detected (such as a human body). From inside to outside are a first detector layer, a second detector layer, and a third detector layer. The 9 detectors include a total of two types of detectors, a first type of detector 1 and a second type of detector 2. Moreover, any two adjacent detectors have different attenuation ratios to the photons.

Specifically, the first detector and the second detector are made of different materials. With the imaging device of this embodiment, a light 3 from a position 5 of the object to be detected O and a light 4 from a position 6 of the object to be detected O respectively pass through the first type of detector 1 and the second type of detector 2 in the first detector layer before being incident on the second type of detector 2 in the second detector layer, which causes different attenuations, so that probabilities of the photons incident on the second type of detector 2 in the second detector layer come from the position 5 and the position 6 are different, thereby playing the role of determining the direction of the photon. The position 5 and the position 6 are two different positions inside the object to be detected O.

It should be noted that, the number of detectors, the number of detector layers, and the number of detector types in this embodiment are merely exemplary descriptions, that is, the number of detectors is not limited to 9, and the number of detector layers is also not limited to three layers, and the types of detectors are not limited to two types, and those skilled in the art may adjust them appropriately as needed.

Embodiment 2

Figure 2:
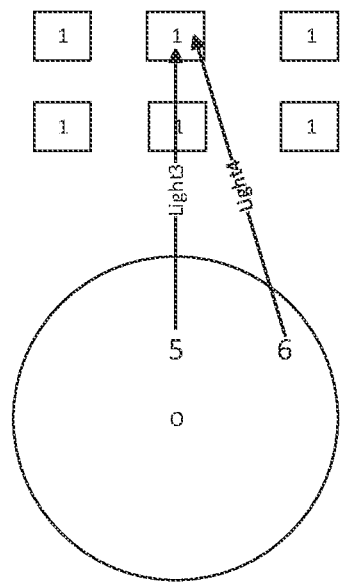
FIG. 2 is a schematic structural diagram of a gamma radiation imaging device according to another embodiment of the present disclosure.

In this embodiment, as shown in FIG. 2, the imaging device includes 6 detectors, and the 6 detectors form 2 detector layers, which are distributed in 2 layers outside the object to be detected (such as a human body). From inside to outside are a first detector layer and a second detector layer. The six detectors are all the first type of detector 1. Moreover, there is a interval between any two adjacent detectors, that is, there is an interval between the first detector layer the second detector layer, there is an interval between two adjacent detectors of the first detector layer, and there is also an interval between two adjacent detectors of the second detector layer.

Specifically, with the imaging device of this embodiment, the light 3 from the position 5 of the object to be detected and the light 4 from the position 6 of the object to be detected before being incident on the detector in the second detector layer, the light 3 from the position 5 of the object to be detected passes through the detector of the first detector layer, and the light 4 from the position 6 of the object to be detected only passes through the air, which causes different attenuations, so that probabilities of the photons incident on the detector in the second detector layer come from the position 5 and the position 6 are different, thereby playing the role of determining the direction of the photon.

It should be noted that, the number of detectors, the number of detector layers, and the number of detector types in this embodiment are merely exemplary descriptions, that is, the number of detectors is not limited to 6, and the number of detector layers is also not limited to two layers, and the type of the detector is not limited to type 1, and those skilled in the art may adjust them appropriately as needed.

In addition, each detector layer of the imaging device of this embodiment may also include multiple types of detectors, and the difference in interval and detector type is used to determine the direction of the photons.

Embodiment 3

Figure 3:
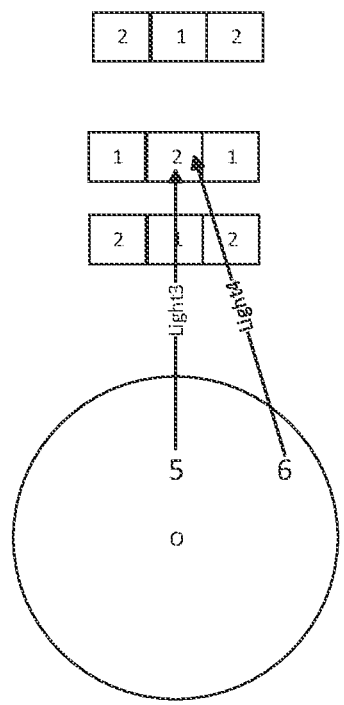
FIG. 3 is a schematic structural diagram of a gamma radiation imaging device according to another embodiment of the disclosure.

In this embodiment, as shown in FIG. 3, the imaging device includes 9 detectors, and the 9 detectors form 3 detector layers, which are distributed in 3 layers outside the object to be detected (such as a human body). From inside to outside are a first detector layer, a second detector layer, and a third detector layer. The 9 detectors include a total of two types of detectors, a first type of detector 1 and a second type of detector 2. There is an interval between two adjacent detector layers, and an interval between the first detector layer and the second detector layer may be different from an interval between the second detector layer and the third detector layer. Any two adjacent detectors have different attenuation ratios to the photons. The layers are separated by a certain distance to further improve the effect of determining the direction of photons.

Specifically, with the imaging device of this embodiment, the light 3 from the position 5 of the object to be detected and the light 4 from the position 6 of the object to be detected before being incident on the second type of detector 2 in the second detector layer, the light 3 from the position 5 of the object to be detected passes through the first type of detector 1 in the first detector layer, and the light 4 from the position 6 of the object to be detected passes through the second type of detector 2 in the first detector layer, which causes different attenuations, so that probabilities of the photons incident on the second type of detector 2 in the second detector layer come from the position 5 and the position 6 are different, thereby playing the role of determining the direction of the photon.

It should be noted that, the number of detectors, the number of detector layers, and the number of detector types in this embodiment are merely exemplary descriptions, that is, the number of detectors is not limited to 9, and the number of detector layers is also not limited to three layers, and the types of detectors are not limited to two types, and those skilled in the art may adjust them appropriately as needed.

Embodiment 4

Figure 4:
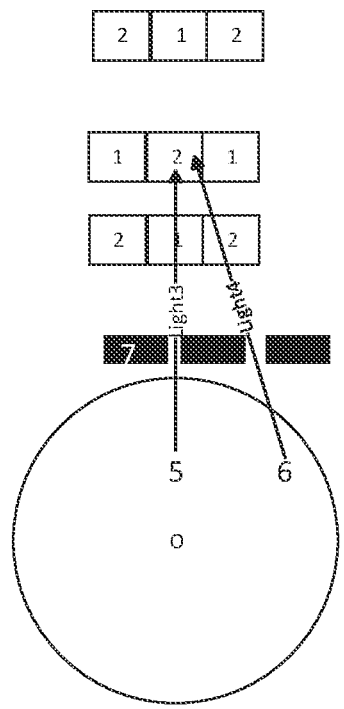
FIG. 4 is a schematic structural diagram of a gamma radiation imaging device according to another embodiment of the disclosure.

In this embodiment, as shown in FIG. 4, the gamma radiation imaging device of the composite detector/collimator includes 9 detectors, and the 9 detectors form 3 detector layers, which are distributed in 3 layers outside the object to be detected (such as a human body). From inside to outside are a first detector layer, a second detector layer, and a third detector layer. The 9 detectors include a total of two types of detectors, the first type of detector 1 and the second type of detector 2. There is an interval between two adjacent detector layers, and an interval between the first detector layer and the second detector layer may be different from an interval between the second detector layer and the third detector layer. Any two adjacent detectors have different attenuation ratios to the photons. The layers are separated by a certain distance to further improve the effect of determining the direction of photons.

Further, the imaging device further includes an absorption collimator 7 with a high aperture ratio between the first detector layer and the object to be detected. In the imaging device of this embodiment, except for the first layer of detectors, the other layers of detectors have the effect of determining the direction of the photons because they are attenuated by the previous layers of detectors. By providing an absorption collimator with a high aperture ratio between the first detector layer and the object to be detected, the effect of determining the direction of the photons by the detectors in the first detector layer is further improved.

It should be noted that, the number of detectors, the number of detector layers, and the number of detector types in this embodiment are merely exemplary descriptions, that is, the number of detectors is not limited to 9, and the number of detector layers is also not limited to three layers, and the types of detectors are not limited to two types, and those skilled in the art may adjust them appropriately as needed.

In addition, this embodiment includes an imaging device with a collimator, and the type and arrangement of the detectors may be the same as those in the previous embodiment, and will not be repeated here.

Embodiment 5

In this embodiment, the gamma radiation imaging device includes a detector unit, and the detector unit includes four detector array layers, which are a first detector array layer, a second detector array layer, a third detector array layer, and the fourth detector array layer. Each detector array layer includes two types of detectors, which are a first detector and a second detector. The first detector includes NaI inorganic scintillator, and the second detector includes LSO inorganic scintillator. In each detector array layer, the first detector and the second detector are arranged alternately. Each first detector in the first detector array layer is opposite to the position of each second detector in the second detector array layer, and each second detector in the first detector array layer is opposite to the position of each first detector in the second detector array layer. The photons emitted from different positions in the object to be detected may pass through the two materials with different attenuation ratios in the detector unit to form different distributions.

Embodiment 6

In this embodiment, the gamma radiation imaging device includes a detector unit, and the detector unit includes four detector array layers, which are a first detector array layer, a second detector array layer, a third detector array layer, and the fourth detector array layer. Each detector array layer includes two types of detectors, which are a first detector and a second detector. The first detector is a GSO detector, and the second detector is an YSO detector. The photons emitted from different positions in the object to be detected may pass through the two materials with different attenuation ratios in the detector to form different distributions.

Embodiment 7

Figure 5:
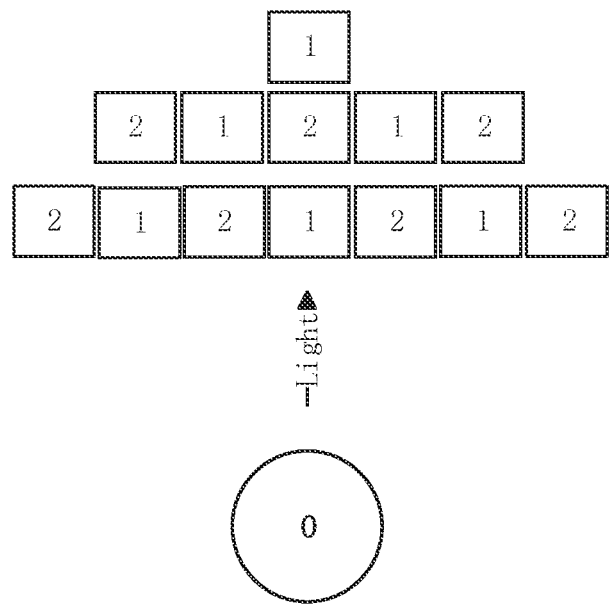
FIG. 5 is a schematic structural diagram of a gamma radiation imaging device according to another embodiment of the disclosure.

In this embodiment, the gamma radiation imaging device includes multiple detector array layers, and each detector array layer includes multiple types of detectors. Where the maximum distance from the object to be detected, that is, the outermost detector array layer includes one type of detector. The detector array layers in the multiple detector array layers except the outermost detector array layer includes multiple types of detectors. The multiple types of detectors in the same detector array layer are arranged alternately, as shown in FIG. 5.

Embodiment 8

Figure 6:
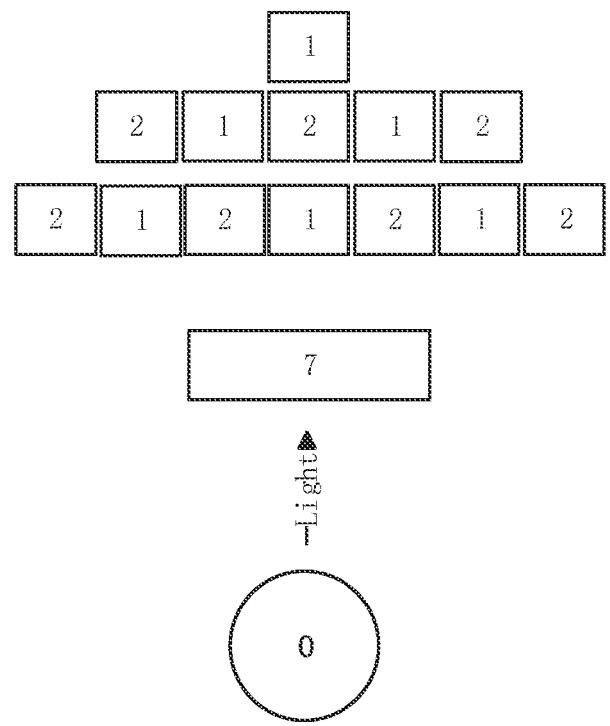
FIG. 6 is a schematic structural diagram of a gamma radiation imaging device according to another embodiment of the disclosure.

The difference from embodiment 7 is that the imaging device of this embodiment further includes a collimator between the first detector layer and the object to be detected, as shown in FIG. 6.

The gamma radiation imaging device adopting the separate detector of the present disclosure has better collimation effect, a greater number of gamma photons are measured, and the spatial resolution and detection efficiency are effectively improved.

In addition, the present disclosure provides an imaging method including:
  providing multiple separate detectors,
  arranging the multiple separate detectors in form of multi-layers outside the object to be detected to form multiple detector layers;
  imaging the object to be detected by using the multiple detector layers.

Rays emitted from different positions in the imaging area reach at least one of the multiple separate detectors through different sets of one or more other detector of the multiple separate detectors, wherein the sets of one or more other detector are different in at least one of thicknesses of detector, materials of detector, and number of detectors.

The present disclosure also provides another imaging method, including:
  providing multiple separate detectors;
  arranging the multiple separate detectors in form of multi-layers outside the object to be detected to form multiple detector layers, wherein two adjacent detector layers are spaced from each other by an interval;
  imaging the object to be detected by using the multiple detector layers.

The present disclosure also provides another imaging method, including:
  providing a collimator and multiple separate detectors including at least two types of detectors;
  arranging the multiple separate detectors in form of multi-layers outside the object to be detected to form multiple detector layers;
  disposing the collimator between the object to be detected and a detector layer located innermost along movement direction of the photons;
  imaging the object to be detected by using the multiple detector layers and the collimator.

The details of the detector, collimator, interval, etc. in the imaging method of the present disclosure are the same as those in the foregoing imaging device embodiment, and will not be repeated here.

It may be seen from the above technical solutions that the gamma radiation imaging device with separate detectors and imaging method of the present disclosure have at least one of the following beneficial effects.

(1) The detector unit used to detect photons may be used as a collimator of other detector units at the same time, so that rays from different directions incident on a certain detector unit may have different attenuation ratios, because they pass through different numbers of other detectors, different thicknesses of other detector units, or different materials of other detector units on their paths, which may reduce the absorption loss of photons on the collimator and improve the effect of determining the direction of the photons and the imaging quality. Therefore, it has both high photon detection efficiency and high photon events information.

(2) The detectors may be divided into multiple layers in space, and by changing the spatial arrangement of the detector units and/or changing the intervals between the detector units, the rays from different directions incident on a certain detector unit may have different attenuation ratios, because they pass through different other detector units on their paths, thereby reducing the absorption loss of photons on the collimator and improving the effect of determining the direction of the photons and the imaging quality.

(3) The detectors may be composed of a variety of materials, and the different photon attenuation ratios of different materials may improve the effect of determining the direction of the photons and the imaging quality, so that the rays from different directions incident on a certain detector unit may have different attenuation ratios, because they pass through different materials of detectors on their paths, thereby reducing the absorption loss of photons on the collimator and improving the effect of determining the direction of the photons and the imaging quality.

In addition, the above definitions of various elements and methods are not limited to the various specific structures, shapes or methods mentioned in the embodiments, and those of ordinary skill in the art may simply modify or replace them.

It should be noted that the directional terms mentioned in the embodiments, such as "upper", "lower", "front", "rear", "left", "right", etc., only refer to the directions of the drawings, and are not used to limit the protection scope of the present disclosure. Throughout the drawings, the same elements are represented by the same or similar reference signs. When it may cause confusion in the understanding of the present disclosure, conventional structures or configurations will be omitted. In addition, the shape and size of each component in the figure do not reflect the actual size and proportion, but merely illustrate the content of the embodiment of the present disclosure. In addition, in the claims, any reference signs between parentheses should not be constructed as limitations on the claims.

Furthermore, the word "comprising" or "including" does not exclude the presence of elements or steps not listed in the claims. The word "a" or "an" preceding an element does not exclude the presence of multiple such elements.

The ordinal numbers used in the description and claims, such as "first", "second", "third", etc., are used to modify the corresponding elements. It does not mean that the element has any ordinal numbers, nor represents the order of a certain element and another element, or the order in the manufacturing method. The use of these ordinal numbers is only used to clearly distinguish one element with a certain name from another element with the same name.

Similarly, it should be understood that in order to streamline the present disclosure and help understand one or more of the various disclosed aspects, in the above description of the exemplary embodiments of the present disclosure, the various features of the present disclosure are sometimes grouped together into a single embodiment, figure, or its description. However, the disclosed method should not be interpreted as reflecting the intention that the claimed disclosure requires more features than the features explicitly recorded in each claim. More precisely, as reflected in the following claims, the disclosure aspect lies in less than all the features of a single embodiment previously disclosed. Therefore, the claims following the specific embodiment are thus explicitly incorporated into the specific embodiment, where each claim itself serves as a separate embodiment of the present disclosure.

The specific embodiments described above further describe the purpose, technical solutions and beneficial effects of the present disclosure in further detail. It should be understood that the above descriptions are only specific embodiments of the present disclosure and are not intended to limit the present disclosure. Any modification, equivalent replacement, improvement, etc., made within the spirit and principle of the present disclosure should be included in the protection scope of the present disclosure.

What is claimed is:

1. A gamma ray imaging device, comprising:
a plurality of separate detectors,
wherein rays emitted from different positions in an imaging area reach at least one of the plurality of separate detectors through different sets of one or more other detectors of the plurality of separate detectors,
wherein the sets of one or more other detector are different in at least one of thickness of detector, material of detector, or number of detectors, and
wherein the plurality of separate detectors are arranged in an array along a movement direction of photons and a direction perpendicular to the movement direction of the photons, and adjacent detectors cause different attenuation ratios to the photons.

2. The imaging device according to claim 1, wherein the rays emitted from different positions received by the at least one of the plurality of separate detectors have different attenuation ratios due to passing through the sets of one or more other detector which are different in at least one of thickness of detector, material of detector, or number of detectors, so as to determine directions of the rays according to the attenuation ratios of the rays.

3. The imaging device according to claim 1, wherein thicknesses of two adjacent detectors of the plurality of separate detectors are different.

4. The imaging device according to claim 1, wherein the plurality of separate detectors comprise at least two detectors arranged along a movement direction of photons, and the at least two detectors comprise a front detector and a rear detector along the movement direction of the photons, and the front detector is configured to block and collimate the photons moving to the rear detector.

5. The imaging device according to claim 1, wherein the plurality of separate detectors form a plurality of detector layers along a movement direction of photons, and one of two adjacent detector layers located on outer side has an area larger than an area of the other one of two adjacent detector layers located on inner side.

6. The imaging device according to claim 5, wherein two adjacent detector layers are spaced from each other by an interval.

7. The imaging device according to claim 6, wherein an interval between two adjacent detector layers of the plurality of separate detector layers is different from an interval between another two adjacent detector layers of the plurality of separate detector layers.

8. The imaging device according to claim 5, wherein the plurality of separate detectors comprises a first type of detectors and a second type of detectors, and the first type of detectors and the second type of detectors are arranged alternately such that a type of one of two adjacent detectors is different from a type of the other of two adjacent detectors.

9. The imaging device according to claim 8, wherein each of the first type and the second type is any one of NaI, CsI, BGO, LSO, LYSO, GSO, YSO, CZT, YAP, or GAGG.

10. The imaging device according to claim 7, wherein distance between any two of the plurality of detectors is configured to cause the photons incident on a detector from different directions to have different attenuation ratios.

11. The imaging device according to claim 6, wherein distance between any two of the plurality of detectors is configured to cause the photons incident on a detector from different directions have different attenuation ratios.

12. The imaging device according to claim 1, wherein two adjacent detectors are spaced from each other by an interval.

13. The imaging device according to claim 12, wherein an interval between two adjacent detectors of the plurality of separate detectors is different from an interval between another two adjacent detectors of the plurality of separate detectors.

14. The imaging device according to claim 1,
wherein a plurality of detector layers are respectively a first detector layer to an $N^{th}$ detector layer, $N>2$,
wherein the first detector layer to the $N^{th}$ detector layer are arranged along the movement direction of photons, and
wherein the imaging device further comprises an absorption collimator between the first detector layer and an object to be detected.

15. An imaging method of the imaging device according to claim 1, the method comprising:
providing a plurality of separate detectors;

arranging the plurality of separate detectors in form of multi-layers outside an object to be detected to form a plurality of detector layers; and imaging the object to be detected by using the plurality of detector layers, wherein rays emitted from different positions in an imaging area reach at least one of the plurality of separate detectors through different sets of one or more other detector of the plurality of separate detectors, wherein the sets of one or more other detector are different in at least one of thickness of detector, material of detector, or number of detectors.

16. An imaging device, comprising:

a plurality of separate detectors, wherein the plurality of separate detectors form a plurality of detector layers arranged outside an object to be detected, wherein two adjacent detector layers are spaced from each other by an interval, and wherein the plurality of separate detectors are arranged in an array along a movement direction of photons and a direction perpendicular to the movement direction of the photons, and adjacent detectors cause different attenuation ratios to the photons.

17. An imaging method of the imaging device according to claim 15, the method comprising:

providing a plurality of separate detectors;

arranging the plurality of separate detectors in form of multi-layers outside an object to be detected to form a plurality of detector layers, wherein two adjacent detector layers are spaced from each other by an interval; and imaging the object to be detected by using the plurality of detector layers.

18. An imaging device, comprising:

a plurality of separate detectors, wherein the plurality of separate detectors comprise at least two types of detectors, wherein the plurality of separate detectors form a plurality of detector layers arranged outside an object to be detected, and wherein the imaging device further comprises a collimator located between the object to be detected and a detector layer located innermost along movement direction of photons, and wherein the plurality of separate detectors are arranged in an array along a movement direction of photons and a direction perpendicular to the movement direction of the photons, and adjacent detectors cause different attenuation ratios to the photons.

19. An imaging method of the imaging device according to claim 16, the method comprising:

providing a collimator and at least two types of a plurality of separate detectors;

arranging the plurality of separate detectors in form of multi-layers outside an object to be detected to form a plurality of detector layers;

disposing the collimator between the object to be detected and a detector layer located innermost along movement direction of photons; and imaging the object to be detected by using the plurality of detector layers and the collimator.

* * * * *